United States Patent [19]

Sheumaker

[11] Patent Number: 4,762,709

[45] Date of Patent: Aug. 9, 1988

[54] LIQUID PROLONGED RELEASE PHARMACEUTICAL FORMULATIONS CONTAINING IONIC CONSTITUENTS

[75] Inventor: Jerry L. Sheumaker, Fairport, N.Y.

[73] Assignee: Pennwalt Corporation, Philadelphia, Pa.

[21] Appl. No.: 825,681

[22] Filed: Jan. 31, 1986

Related U.S. Application Data

[63] Continuation of Ser. No. 532,864, Sep. 16, 1983, abandoned.

[51] Int. Cl.$^4$ .............................................. A61K 31/74
[52] U.S. Cl. ........................................ 424/79; 424/479; 424/483
[58] Field of Search .......................... 424/79, 479, 483

[56] References Cited

U.S. PATENT DOCUMENTS

| | | | |
|---|---|---|---|
| 2,990,332 | 6/1961 | Keating | 167/65 |
| 3,035,979 | 5/1962 | Hays | 424/79 |
| 3,035,984 | 5/1962 | Mierswa | 424/79 |
| 3,051,623 | 8/1962 | Hays et al | 424/79 |
| 3,096,241 | 7/1963 | Hays et al. | 424/79 |
| 3,138,525 | 6/1964 | Koff | 165/55 |
| 3,143,465 | 8/1964 | Keating | 424/79 |
| 3,499,960 | 3/1970 | Macek | 424/33 |
| 3,594,470 | 7/1971 | Borodkin et al. | 424/32 |
| 4,221,778 | 9/1980 | Raghunathan | 424/79 |

FOREIGN PATENT DOCUMENTS

| | | |
|---|---|---|
| 279802 | 3/1970 | Austria . |
| 729827 | 3/1969 | Belgium . |
| 2246037 | 2/1975 | Fed. Rep. of Germany . |

OTHER PUBLICATIONS

Borodkin et al., "Polycarboxylic Acid Ion-Exchange Resin Adsorbates for Taste Coverage in Chewable Tablets", Journal of Pharmaceutical Sciences, vol. 60, No. 10, Oct. 1971, pp. 1523–1527.

*Primary Examiner*—Leonard Schenkman

[57] ABSTRACT

A formulation of a drug wherein the drug is present as a coated, drug-resin complex suspended in a liquid carrier which carrier also contains a second ionic component bearing the same charge as the coated complexed drug, the second ionic component being present as an uncoated, insoluble drug-resin complex.

17 Claims, No Drawings

LIQUID PROLONGED RELEASE PHARMACEUTICAL FORMULATIONS CONTAINING IONIC CONSTITUENTS

This application is a continuation of application Ser. No. 532,864 filed Sept. 16, 1983, now abandoned.

The present invention relates to a liquid form of prolonged continuous release pharmaceutical formulations containing ionic components. More particularly, the invention relates to such formulations wherein the prolonged release of the active drug is accomplished by providing a semi-permeable coating around discrete, minute, ion exchange resin particles with which the drug component has been reacted to form an insoluble drug-resin complex. The semi-permeable coating creates a diffusion barrier, the thickness of which can be adjusted to provide the desired level of retardation of drug availability in the gastrointestinal tract over a period of time. The preparation of typical coated, insoluble drug-polymer complexes is disclosed in detail and claimed in U.S. Pat. No. 4,221,778 dated Sept. 9, 1980 to Raghunathan. Drugs utilizing the Raghunathan delivery system may be administered in either capsule or liquid suspension form. The feasibility of liquid dosage is a particularly important advantage of the Raghunathan invention because most commercial sustained release systems require solid coatings whose rate of solution controls drug availability, thereby precluding administration in liquid form. Nevertheless, in attempts to provide formulations using Raghunathan's coated, insoluble drug-resin complexes it was observed that the presence of ionic substances in the formulation at times disturbed the expected dissolution profile for the coated drug-resin complex. The problem was observed to be particularly accute when attempts were made to provide formulations of combination type drugs where each drug was ionic and of the same ionic charge and where at least one drug was present in the coated, drug-resin complex form while at least one other (usually present in very minor amounts) was present in its ionic form. The present invention addresses this problem by providing that substantially all ionic components in a formulation of the Raghunathan sustained release drug type, which component bears the same ionic charge as the drug on the coated, drug-resin complex be present as a resin complex.

PRIOR ART

In addition to the Raghunathan patent identified above, various coated resins and drug-resin complexes have been reported (e.g., in U.S. Pat. Nos. 3,138,525; 3,499,960 and 3,594,470; Belgian Pat. No. 729,827; German Pat. No. 2,246,037; and Brodkins et al, Journal of Pharmaceutical Science, Vol. 60, pages 1523–1527, 1971), but none suggest a solution to the problem disclosed herein.

BRIEF SUMMARY OF THE INVENTION

The present invention provides a formulation of a drug wherein the drug is present as a coated, drug-resin complex suspended in a liquid carrier which carrier also contains a second ionic component bearing the same charge as the coated complexed drug, the second ionic component being present as an uncoated, insoluble drug-resin complex. While applicant does not wish to be bound by any theory of operation, it is postulated that when the second ionic component of like charge to the coated drug is present in a formulation, the unbound ion penetrates the diffusion barrier and, to some degree, exchanges upon the resin particle with the drug previously bound thereby causing an increase in the amount of unbound drug in the formulation as well as producing a change in the dissolution profile (i.e. the amount of drug in solution versus time) of the previously bound drug; solution of the problem is accomplished by binding the second ionic component to its own resin.

DETAILED DESCRIPTION

Pursuant to Raghunathan U.S. Pat. No. 4,221,778 it has been found that a selective, prolonged continuous release of pharmacologically active drugs, under conditions such as those encountered in the gastrointestinal tract, can be achieved by the application of a diffusion barrier coating to an ion exchange drug-resin complex particle which has been treated with a solvating agent; the present invention provides an improvement whereby prolonged release formulations from coated drugs of the Raghunathan type can be prepared under circumstances wherein a component of the formulation contains a second ionic substance (e.g. a combination drug, a dye, a dispersing agent or the like) bearing the same ionic charge as the drug on the drug-resin complex by employing the second ionic substance in the ion form of an exchange resin complex. The manufacture of a formulation of any drug for liquid dosage usage requires that the final formulation have the drug dissolved or suspended in a liquid that is pleasing to the eye and taste, possess extended shelf-life stability, and exhibit no change in active drug dosage level over a period of time. Thus, to prepare a liquid formulation of any type drug, including one of the Raghunathan type, it is necessary to employ extenders such as water or syrup, and to add flavors, sweeteners, thickening agents, dyes, and the like. Since the presence of these non-biologically active components in contact with the semi-permeable membranes taught by Raghunathan will often have some effect on the ability of the active drug to escape in the digestive system from the ion complex upon which it is held it is essential that the dissolution profile of the particular drug system (i.e. the amount of drug released over stated periods of time) be measured in the formulation in which one intends to administer a particular dosage. From time to time in the transition of the Raghunathan products from the laboratory to commercial embodiments, erratic results have been obtained in the dissolution profile of the formulation versus the dissolution profile of the same drug in water. It was determined that one source of such erratic results was the presence of ionic substances bearing the same ionic charge as the sustained release drug present in the formulation as a coated drug-resin complex; the presence of ionic substances of opposite charge appear to have no effect on the expected dissolution rate. Pursuant to the present invention it was found that if the second ionic substance of the same charge is bound upon a resin complex of its own, the erratic results are largely eliminated. Resins suitable for binding the second ionic component may be any of those previously disclosed in the Raghunathan patent. Obviously, the second ionic material need not be coated with the water-permeable diffusion barrier coating taught in Raghunathan.

ILLUSTRATIVE EXAMPLES

The following examples are cited to illustrate the invention. They are not intended to limit it in any fashion.

Example I

A Raghunathan type prolonged release coated, drug resin complex was prepared from pseudoephedrine generally following Example 20 of the Raghunathan patent. A formulation was prepared from 49.7 gm. of the coated, drug resin complex using approximately 600 ml. of xanthan gum, pregelatinized starch and water as the suspending agent. Also included in the composition was an aqueous solution of a dye, 400 gm. of granulated sugar and corn syrup, a wetting agent (propylene glycol), and, in very small quantities, a preservative and flavorings. A sample of this formulation was withdrawn and tested in various intervals to determine the availability of the pseudoephedrine under conditions which would be encountered in the digestive system. The results obtained appear as Column A in Table I.

In an attempt to prepare a combination drug of pseudoephedrine and chlorpheniramine, 1.2 gm. of chlorpheniramine maleate was added to a formulation substantially identical to the above (except for dyes and flavorings). A sample of the combination drug formulation was analyzed to provide the dissolution profile of pseudoephedrine which is reported in Table I, Column B. A comparison of the results shown in Columns A and B discloses a substantial decrease in the availability of pseudoephedrine during the first hour and a half after dosage and a substantial increase in availability thereafter as compared with the results obtained with pseudoephedrine alone.

In a third embodiment the same amount of chlorpheniramine maleate as used above was added in the form of a resin complex, using the same resin (Amberlite XE-69) employed to complex the pseudoephedrine. A small sample examined for the dissolution profile of pseudoephedrine produced the result shown in Column C of Table I. It will be obvious from the table that when the second ionic component is added in the form of the resin complex there is substantially no disturbing effect upon the dissolution profile of the ephedrine.

TABLE I

| Interval (Hrs.) | Pseudoephedrine Availability (%) | | |
|---|---|---|---|
| | A | B | C |
| ½ | 49.9 | 23.1 | 51.6 |
| 1 | 53.4 | 28.7 | 53.5 |
| 3 | 66.5 | 78.8 | 64.9 |
| 6 | 73.9 | 87.8 | 72.3 |

Example II

Not only is the dissolution profile of the coated drug resinate changed when a second drug is present in ionic form in the same formulation versus the same combination when the second drug is in the form of a drug resinate, but the dissolution rate of the second drug also varies under such circumstances. Thus from the dissolution results of Table II, wherein codeine (as a coated drug resinate) in substantially the same formulation suspension as taught in Example I is present with chlorpheniramine, (in ionic form in Run E but present in drug resinate form in Run D) it can be seen that the presence of the chlorpheniramine (second component) in its ionic form retards the availability of each of the drugs over the period of observation.

TABLE II

| Interval (Hrs.) | Codeine | | Chlorpheniramine | |
|---|---|---|---|---|
| | $D^{xx}$ | $E^*$ | $D^{xx}$ | $E^*$ |
| 0.5 | 31.2 | 24.0 | 48.7 | 34.9 |
| 1.0 | 35.4 | 29.5 | 57.4 | N.M. |
| 3.0 | 44.0 | 40.2 | 69.7 | 58.9 |
| 6.0 | 49.9 | 48.1 | 77.0 | N.M. |

N.M. indicates value not measured.
*Chlorpheniramine present in ionic form.
xxChlorpheniramine present in drug-resinate form.

In the embodiment of this example the coated codeine-resinate (prepared in the manner taught for pseudoephedrine in Example I) was used in an amount of 17.7 gm.; the chlorpheniramine was present in an amount of 0.80 gm. In the resinated form the chlorpheniramine was bound to Amberlite XE-69 resin.

Another typical combination to which the present invention is applicable is hydrocodone and chlorpheniramine where the hydrocodone is present in the coated, hydrocodone-resinate form.

While the present invention is of particular importance in the formulation of ionic type combination drugs, it will be obvious that it can be employed to control the erratic dissolution characteristics of single ionic drugs from formulations containing any extraneous ionic material. For instance, the erratic dissolution problem can be caused by the presence of a dye of appropriate ionic charge; pursuant to the present invention the dye would be complexed with a resin prior to addition to the formulation. The types of medications that could be useful in combined form in the present invention are many, thus combinations of any of the following are possible: analgesics, decongestants, anorexics, antiarthritics, antiasthmas, antibiotics, antidepressants, antihypertensives, antiinflammatories, antipsychotics, antispasmotics, anticholinergics, and muscle relaxants.

Many equivalent modifications of this invention will become apparent to those skilled in the arts from a reading of the above without help from the inventive concept.

What is claimed:

1. A formulation of an ionic drug wherein the drug is present as a component of a coated drug-resin complex suspended in a liquid carrier which carrier also contains a second ionic component bearing the same charge as the coated complexed drug, the second ionic component being present as a component of an uncoated resin complex, the resin particle of the coated drug-resin complex being an ion exchange resin having been treated in an amount sufficient to retard its rate of swelling in water with an impregnating agent selected from the group consisting of polyethylene glycol, propylene glycol, mannitol, lactose and methylcellulose, and which treated particle has been subsequently coated with a water-permeable diffusion barrier, the second ionic component being present in an amount that would disturb the dissolution profile of the coated drug-resin complex if that amount was present in unbound form instead of as a component of an uncoated resin complex, and the resin of the uncoated resin particle being an ion exchange resin present in an amount that is sufficient to bind the second ionic component but is not so large as to disturb the dissolution profile of the coated drug-resin complex.

2. The formulation of claim 1 wherein the second ionic component is a drug.

3. The formulation of claim 2 wherein the drug in the coated drug-resin complex is codeine.

4. The formulation of claim 3 wherein the second ionic component is chlorpheniramine.

5. The formulation of claim 2 wherein the drug in the coated drug-resin complex is pseudoephedrine.

6. The formulation of claim 5 wherein the second ionic component is chlorpheniramine.

7. The formulation of claim 2 wherein the drug in the coated drug-resin complex is hydrocodone.

8. The formulation of claim 7 wherein the second ionic component is chlorpheniramine.

9. A pharmaceutical composition, comprising:
an ionic drug adsorbed on ion exchange resin particles to form a coated drug-resin complex, said ion exchange resin particles of the coated drug-resin complex having been treated with an impregnating agent selected from the group consisting of polyethylene glycol, propylene glycol, mannitol, lactose and methylcellulose in an amount sufficient to retard the rate of swelling in water and subsequently coated with a water-permeable diffusion barrier;
a second ionic component bearing the same charge as said ionic drug adsorbed on ion exchange resin particles to form a second ionic component-resin complex, said ion exchange resin particles of the second ionic component-resin complex are uncoated; and
a liquid carrier.

10. A pharmaceutical composition according to claim 9 wherein said second ionic component is a drug.

11. A pharmaceutical composition according to claim 10 wherein the ionic drug in the coated-resin complex is codeine.

12. A pharmaceutical composition according to claim 11 wherein the second ionic component is chlorpheniramine.

13. A pharmaceutical composition according to claim 10 wherein the ionic drug in the coated-resin complex is pseudoephedrine.

14. A pharmaceutical composition according to claim 13 wherein the second ionic component is chlorpheniramine.

15. A pharmaceutical composition according to claim 10 wherein the ionic drug in the coated resin complex is pseudoephedrine.

16. A pharmaceutical composition according to claim 15 wherin the second ionic component is chlorpheniramine.

17. A pharmaceutical composition, comprising:
an ionic drug selected from the group consisting of codeine, pseudoephedrine and hydrocodone adsorbed on ion exchange resin particles to form a coated drug-resin complex, said ion exchange resin particles of the coated drug-resin complex having been treated with an impregnating agent selected from the group consisting of polyethylene glycol, propylene glycol, mannitol, lactose and methylcellulose in an amount sufficient to retard the rate of swelling in water and subsequently coated with a water-permeable diffusion barrier;
chlorpheniramine adsorbed on ion exchange resin particles to form a chlorpheniramine-resin complex, said ion exchange resin particles of the chlorpheniramine-resin complex are uncoated; and
a liquid carrier.

* * * * *